US00PP08982P

United States Patent [19]

VandenBerg

[11] Patent Number: Plant 8,982

[45] Date of Patent: Nov. 15, 1994

[54] CHRYSANTHEMUM PLANT NAMED RAQUEL

[75] Inventor: Cornelis P. VandenBerg, Salinas, Calif.

[73] Assignee: Yoder Brothers, Inc., Barberton, Ohio

[21] Appl. No.: 169,190

[22] Filed: Dec. 20, 1993

[51] Int. Cl.[5] ..... A01H 5/00

[52] U.S. Cl. ..... Plt./82

[58] Field of Search ..... Plt. 82, 76

*Primary Examiner*—Howard J. Locker

*Attorney, Agent, or Firm*—Foley & Lardner

[57] ABSTRACT

A Chrysanthemum plant named Raquel particularly characterized by its flat capitulum form; decorative capitulum type; dark red ray floret color; diameter across face of capitulum of 43 to 50 mm when fully opened; branching pattern is spreading, with 7 to 9 breaks after pinch when grown outside under natural daylength in fall flowerings and 6 to 8 breaks when grown in 10 cm pots for spring flowerings; natural season flower date of August 21 to 24 when planting rooted cuttings on June 18 to 19 in Salinas, Calif., and September 30 to October 12 when planting rooted cuttings June 15 to June 18 in Hightstown, N.J.; flowering response of 45 to 51 days after rooting in no light/no shade programs in spring in Salinas; plant height of 30 to 33 cm when grown in fall under natural daylength with no growth regulators in New Jersey, and 13 to 15 cm when grown in 10 cm pots in spring with no growth regulator applications; and recommended as mid-season variety.

3 Drawing Sheets

The present invention comprises a new and distinct cultivar of Chrysanthemum, botanically known as *Dendranthema grandiflora,* and referred to by the cultivar name Raquel.

Raquel, identified as 8798 (90-858002), was originated from a cross made by Cornelis P. VandenBerg in a controlled breeding program in Salinas, Calif. in April 1990.

The female parent of Raquel was the cultivar identified as Bravo, a red decorative garden mum disclosed in U.S. Plant Pat. No. 6,888.

The male parent of Raquel was an unnamed seedling identified as 8882 (87-289003) and described as a purple decorative garden mum with many disc florets. The male parent was discarded from all programs in September 1990.

Raquel was discovered and selected as one flowering plant within the progeny of the stated cross by Cornelis P. VandenBerg in January 1991, in a controlled environment in Salinas, Calif.

The first act of asexual reproduction of Raquel was accomplished when vegetative cuttings were taken from the initial selection in April 1991 in a controlled environment in Salinas, Calif., by technicians working under supervision of Cornelis P. VandenBerg.

Horticultural examination of controlled flowerings of successive plantings has shown that the unique combination of characteristics as herein disclosed for Raquel are firmly fixed and are retained through successive generations of asexual reproduction.

Raquel has not been observed under all possible environemental conditions. The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial greenhouse practice for small pot spring garden mum production.

The following traits have been repeatedly observed and are determined to be basic characteristics of Raquel, which, in combination, distinguish this Chrysanthemum as a new and distinct cultivar:

1. Flat capitulum form.
2. Decorative capitulum type.
3. Very dark red ray floret color.
4. Diameter across face of capitulum of 43 to 50 mm when fully opened.
5. Branching pattern is spreading, with 7 to 9 breaks after pinch when grown outside under natural daylength in fall flowerings and 6 to 8 breaks when grown in 10 cm pots for spring flowerings.
6. Natural season flower date of August 21 to 24 when planting rooted cuttings on June 18 to 19 in Salinas, Calif., and September 30 to October 12 when planting rooted cuttings June 15 to June 18 in Hightstown, N.J.
7. Flowering response of 45 to 51 days after rooting in no light/no shade programs in spring in Salinas.
8. Plant height of 30 to 33 cm when grown in fall under natural daylength with no growth regulators in New jersey, and 13 to 15 cm when grown in 10 cm pots in spring with no growth regulator applications.
9. Recommended as mid-season variety.

The accompanying photographic drawings show typical inflorescence and leaft charactereistics of Raquel, with the colors being as nearly true as possible with illustrations of this type.

Sheet 1 is a color photograph of Raquel grown outside in Salinas, Calif. and dug and transplanted into 15 cm bulb pans at flowering time for photography purposes.

Sheet 2 is a black and white photograph of three views of the inflorescence of Raquel. Sheet 3 is a black and white photograph showing the upper and under sides of the leaves of Raquel at 3 stages of development (mature, intermediate and immature). In sheets 2 and 3 a measuring tape in centimeters has been added.

Of the commercial cultivars known to the inventor, the most similar in comparison to Raquel is the cultivar identified as Bravo, disclosed in U.S. Plant Pat. No. 6,888. Reference is made to attached Chart A, which compares certain characteristics of Raquel to the same characteristics of Bravo.

Similar traits are capitulum form and type. The ray floret color of both Raquel and Bravo is generally described as red, but Raquel has a darker red ray floret color than Bravo. The diameter across face of capitulum of Raquel and Bravo is comparable. Raquel has a later natural season flower date than Bravo in both Salinas and Hightstown, and a slower controlled flowering response in spring and shorter plant height than Bravo. In addition, when planted outside in the fall, Bravo shows a rapid fading to brown-red, while the fading of Raquel is much slower, fading to a bluish red.

In the following description, color references are made to The Royal Horticultural Society Colour Chart. The color values were determined on plant material grown as a pinched garden mum grown outdoors in Salinas, Calif. on Aug. 16, 1993.

Classification:

*Botanical.*—*Dendranthema grandiflora* cv Raquel.

*Commercial.*—Flat decorative spray pot mum and garden mum.

INFLORESCENCE

A. Capitulum:

*Form.*—Flat.

*Type.*—Decorative.

*Diameter across face.*—43 to 50 mm when fully opened.

B. Corolla of ray florets:

*Color (general tonality from a distance of three meters).*—Very dark red.

*Color (upper surface).*—Between 53A and 185A.

*Color (under surface).*—185C to 185D, petal tips overlaid with 185A.

*Shape.*—Cross section of inner ray florets straight, outer ray florets convex. Petal tips rounded.

C. Corolla of Disc Florets:

*Color (mature).*—14B.

*Color (immature).*—14B, slightly overlaid with 144B.

D. Reproductive organs:

*Androecium.*—Present on disc florets only; scant pollen.

*Gynoecium.*—Present on both ray and disc florets.

PLANT

A. General Appearance:

*Height.*—30 to 33 cm when grown in fall under natural daylength in New Jersey with no growth regulators, and 13 to 15 cm when grown in 10 cm pots in spring with no growth regulator applications.

*Branching pattern.*—Spreading, with 7 to 9 breaks after pinch when grown outside under natural daylength in fall flowerings and 6 to 8 breaks when grown in 10 cm pots for spring flowerings.

B. Foliage:

*Color (upper surface).*—147A.

*Color (under surface).*—147B.

*Shape: See photograph.*

CHART A

| | RAQUEL | BRAVO |
|---|---|---|
| Ray floret color | Dark Red | Red |
| Capitulum form and type | Flat decorative | Flat decorative |
| Diameter across face of capitulum | 43 to 50 mm | 45 to 50 mm |
| Natural season flower date: | | |
| in Salinas, CA | Aug 21 to 24 | Aug 16 to 23 |
| in Highstown, NJ | Sep 30 to Oct 12 | Sep 12 to Oct 1 |
| Controlled response | 45 to 51 days | 45 to 46 days |
| Plant height: | | |
| in natural season fall | 30 to 33 cm | 33 to 36 cm |
| in 10 cm pots spring | 13 to 15 cm | 18 to 23 |

COMPARISONS MADE OF PLANTS GROWN UNDER NATURAL SEASON OUTDOOR CONDITIONS IN SALINAS, CALIFORNIA AND IN HIGHTSTOWN, NEW JERSEY AND IN SPRING FLOWERING PROGRAMS IN SALINAS, CALIFORNIA

I claim:

1. A new and distinct Chrysanthemum plant named Raquel, as described and illustrated.

* * * * *

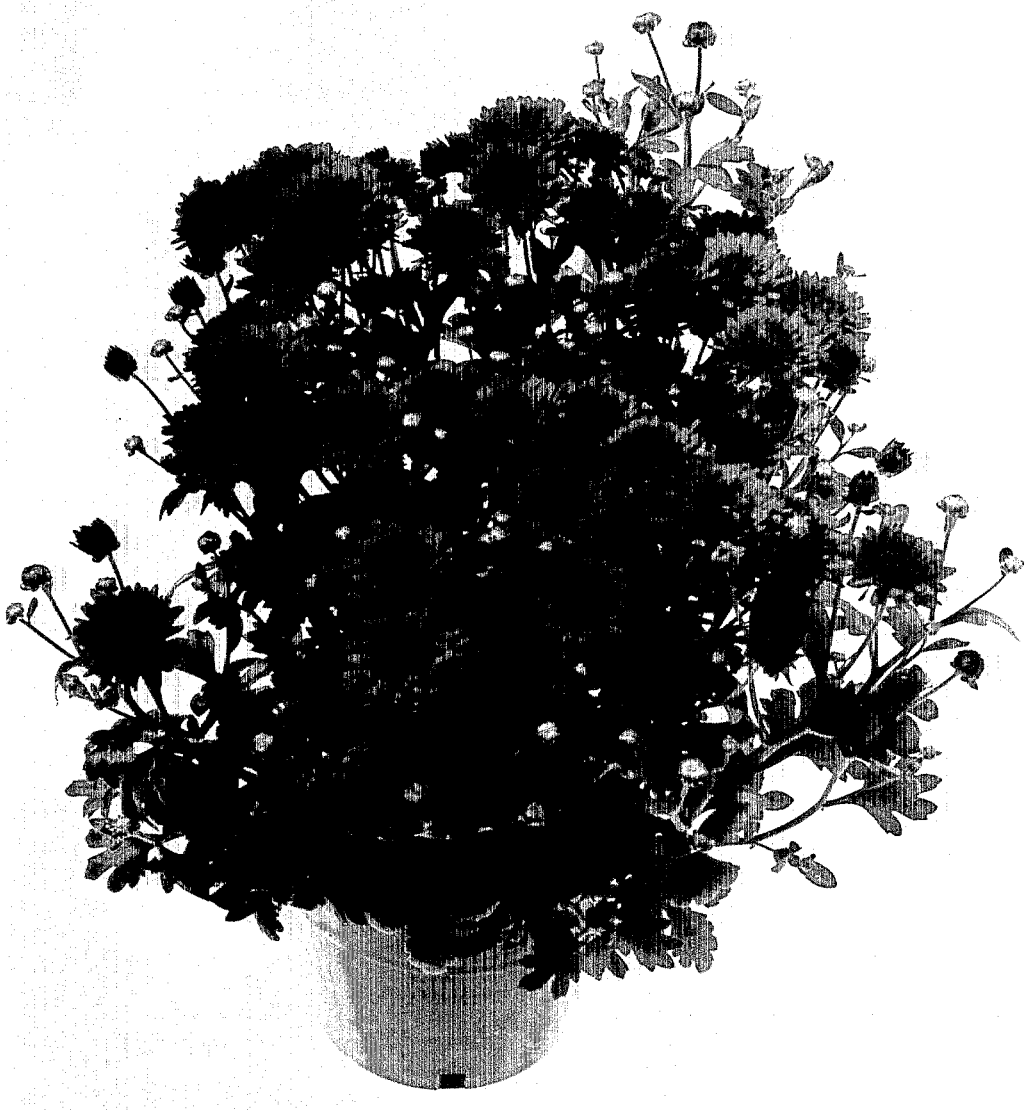

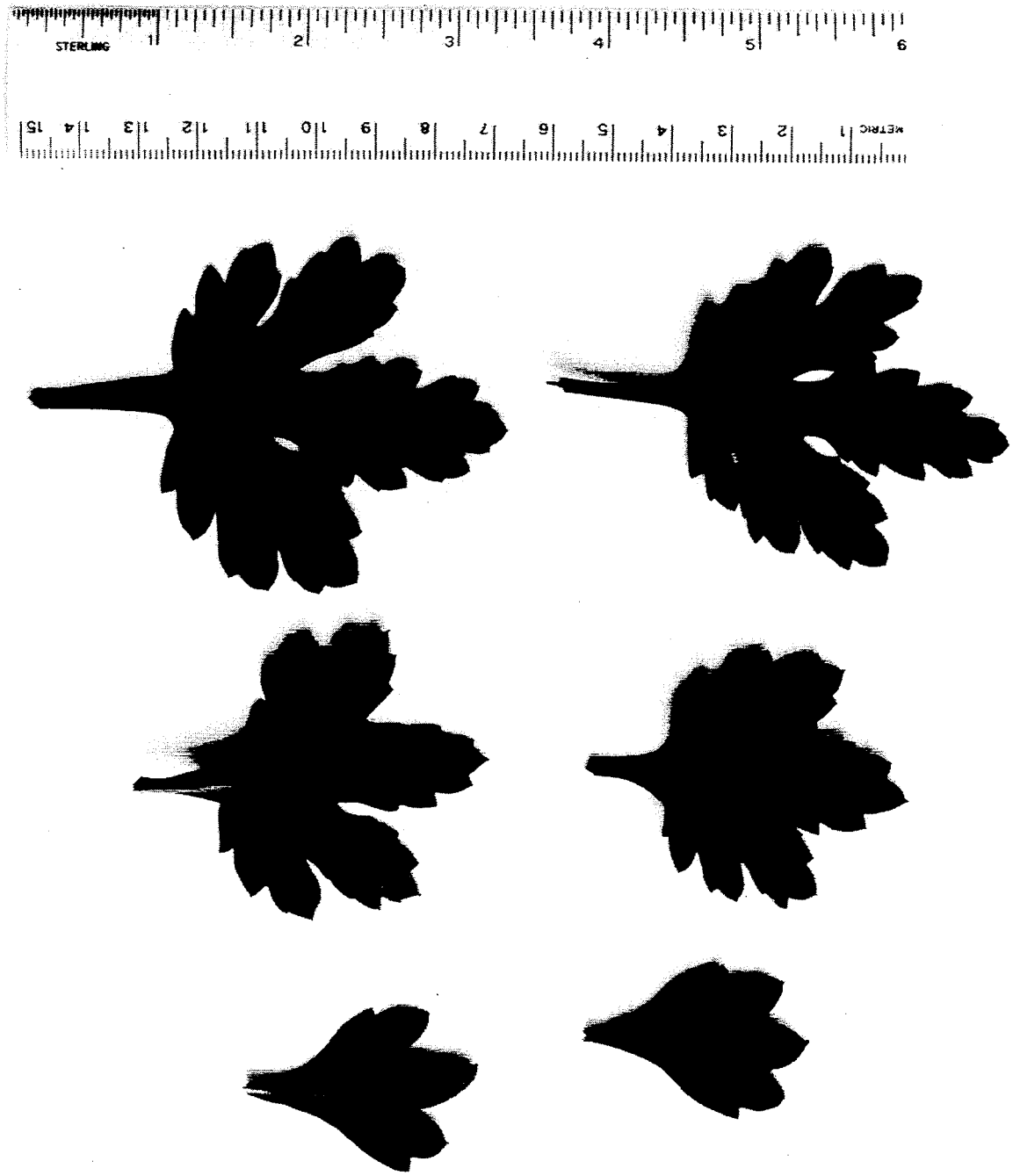
STERLING
METRIC

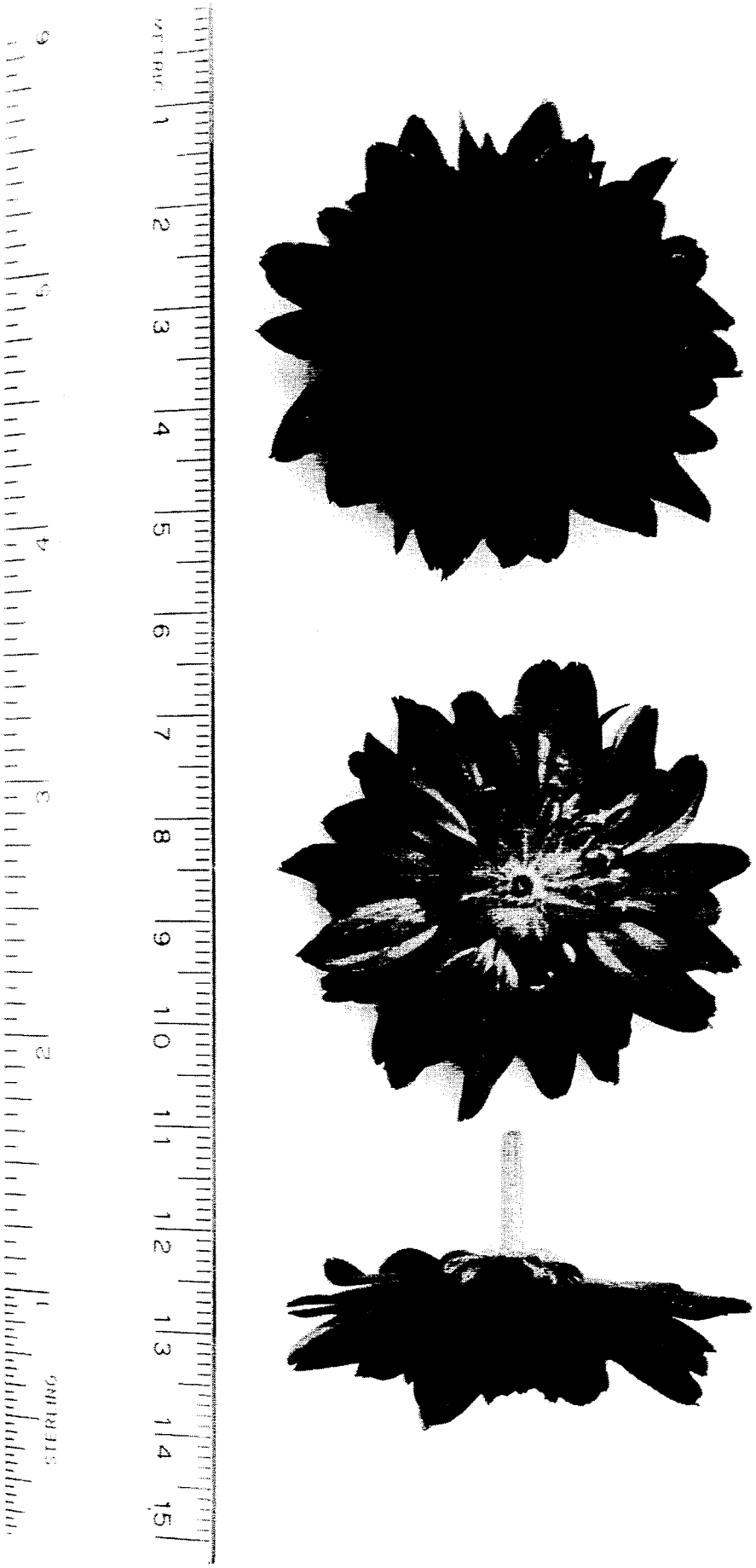
INCHES
1 2 3 4 5 6 7 8 9 10 11 12 13 14 15
INCHES
1 2 3 4 5 6